(12) United States Patent
Thomsen et al.

(10) Patent No.: US 6,573,988 B1
(45) Date of Patent: Jun. 3, 2003

(54) CUVETTE AND SPACER THEREFOR AS WELL AS A METHOD OF PRODUCING THE SPACER

(75) Inventors: Henrik Thomsen, Hillerød (DK); Henning Gråskov, Bagsværd (DK)

(73) Assignee: Foss Electric A/S, Hillerød (DK)

( * ) Notice: Subject to any disclaimer, the term of this patent is extended or adjusted under 35 U.S.C. 154(b) by 0 days.

(21) Appl. No.: 09/509,873

(22) PCT Filed: Oct. 30, 1998

(86) PCT No.: PCT/DK98/00473

§ 371 (c)(1),
(2), (4) Date: Apr. 3, 2000

(87) PCT Pub. No.: WO99/23473

PCT Pub. Date: May 14, 1999

(30) Foreign Application Priority Data

Oct. 31, 1997 (DK) .............................. PCT/DK97/00492

(51) Int. Cl.$^7$ ............................ G01N 1/10; G01N 21/01
(52) U.S. Cl. ....................................... 356/246; 356/244
(58) Field of Search ................................ 356/246, 244; 436/517; 250/390.11; 600/108–110

(56) References Cited

U.S. PATENT DOCUMENTS

| 4,560,269 A | 12/1985 | Baldszun et al. |
|---|---|---|
| 5,003,174 A | 3/1991 | Datwyler et al. |
| 5,112,453 A | 5/1992 | Behr et al. |
| 5,347,358 A * | 9/1994 | Nebe et al. ............... 356/128 |

FOREIGN PATENT DOCUMENTS

| SE | C2502995 | 3/1996 |
|---|---|---|
| WO | WO 9601417 | 1/1996 |
| WO | WO 9820338 | 5/1998 |

* cited by examiner

Primary Examiner—Georgia Epps
Assistant Examiner—M. Abutayeh
(74) Attorney, Agent, or Firm—Birch, Stewart, Kolasch & Birch, LLP

(57) ABSTRACT

A cuvette for a spectrometric analysis instrument has two opposing windows made of a material, which is transparent to the light of the waveband used for the analysis. The windows define a limited light path of a light beam passing through a cavity inside the cuvette. When using cuvettes having windows of a material, such as diamond, having a refractive index considerably different from the fluid to be analyzed, the window surfaces forming the cuvette cavity should not be parallel, thereby ensuring that the internal distances between opposed areas of the window surfaces will vary across the transparent windows. Thereby any internal reflections within the cavity will add in almost random phase, avoiding any tendency to resonance. This is very advantageous when the instrument is a member of a plurality of instruments, which must be standardized in order to be able to provide uniform calibrations for said plurality of instruments.

9 Claims, 5 Drawing Sheets

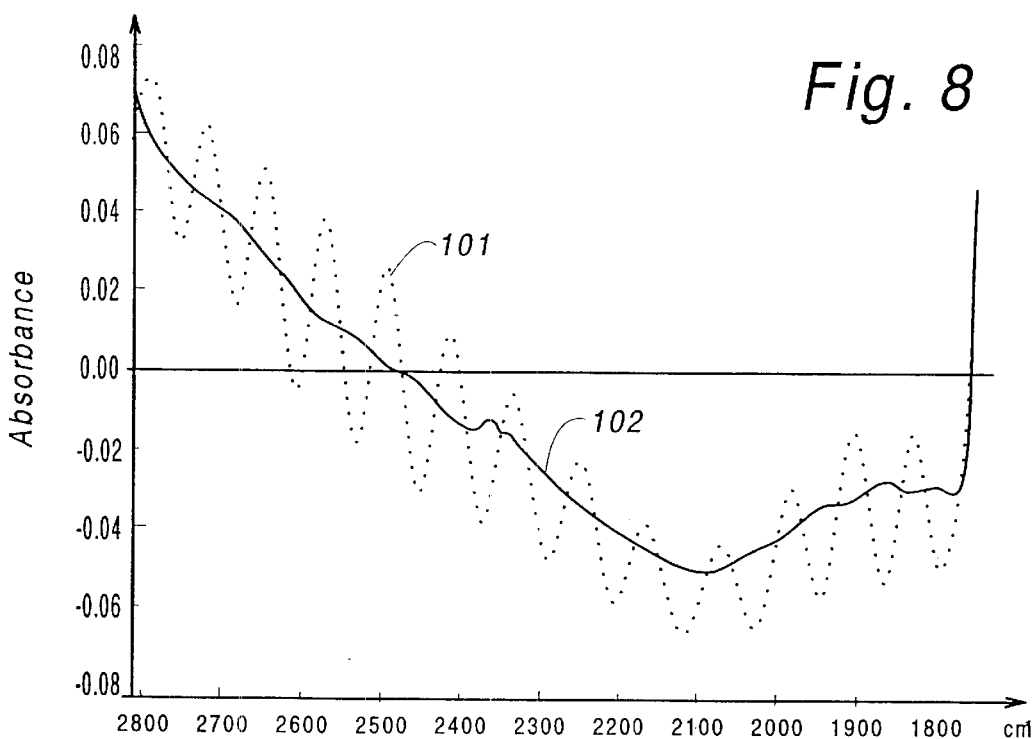
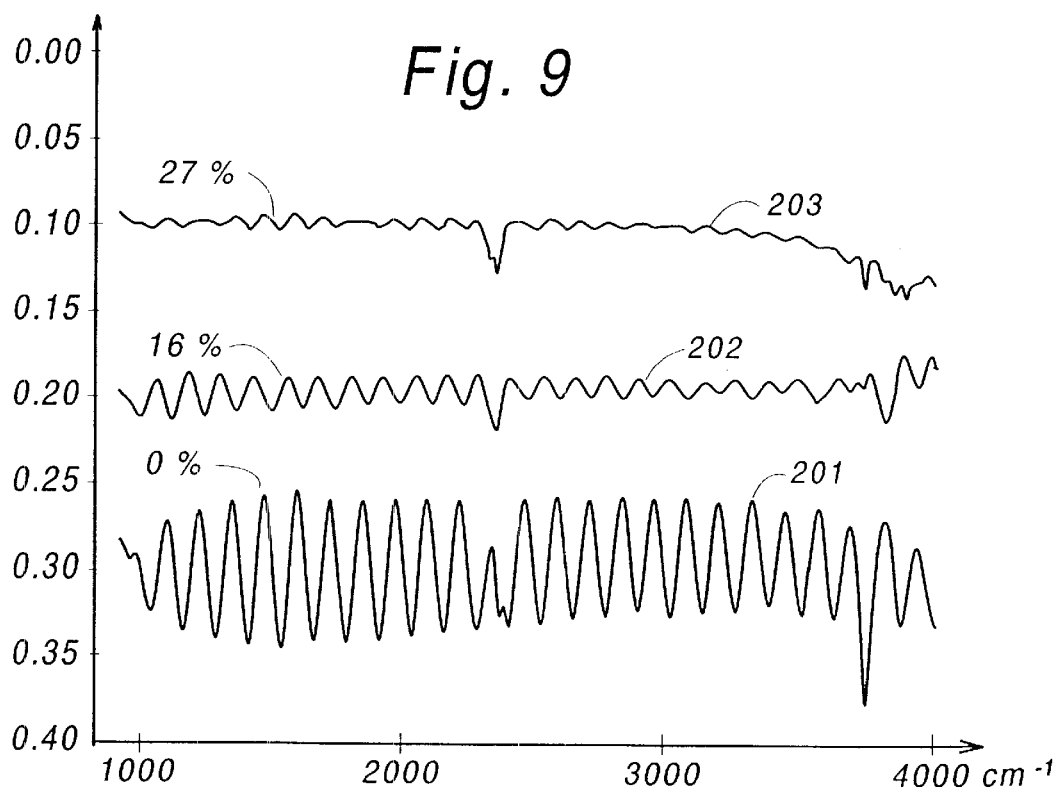

CUVETTE AND SPACER THEREFOR AS WELL AS A METHOD OF PRODUCING THE SPACER

This application is the national phase under 35 U.S.C. §371 of PCT International Application No. PCT/DK98/00473 which has an International filing date of Oct. 30, 1998, which designated the United States of America.

TECHNICAL FIELD

The present invention relates to a cuvette for a spectrometric analysis equipment, said cuvette having two opposing windows made of a material, which is transparent to the light of the waveband used for the analysis, said windows defining a limited light path of a light beam passing through a cavity inside the cuvette. More specifically the invention relates to a cuvette used in spectrometric equipment such as interferometers, essentially for analysis of fluid samples. Further, the invention relates to a spacer for the cuvette and a method for producing the spacer.

BACKGROUND ART

Generally, presently used cuvettes apply parallel windows. A method and flow system for spectrometry and a cuvette is disclosed in DK patent application No. 1221/96 and in the corresponding WO 98/20338. A cuvette having a wedge shaped spacer is claimed in WO 98/20338.

The Problem

The present invention specifically relates to spectroscopic equipment for analysis of milk. Such equipment uses fairly thin cuvettes having light paths of typically about 15–50 $\mu$m. Optical cuvettes used for high pressures and dedicated to have a long life in flow systems in which they are highly exposed to intensive wear may advantageously be provided with diamond windows. Due to considerable differences in refractive indexes between fluid in the cuvette and the diamond windows the light beam may be subjected to multiple reflections, i.e. the cuvette may become a resonator. Such reflections and resonance will influence the recorded spectra as explained further in the detailed specification. This poses a problem when it is the intention to produce and distribute a great number of IR measurement instruments. In this respect, it is essential to be able to transfer standard calibrations to such instruments. Otherwise, it would be necessary to perform individual calibrations on each of the instruments. Such calibrations are time-consuming. Accordingly, it is essential to be able to standardise all instruments, a process, which may be performed by measuring a standard fluid on the instrument, and adjusting the instrument to give a predetermined response. Experience has shown that multiple reflections occurring in the cuvettes having substantially parallel diamond windows obstruct the use of standard calibrations. Accordingly it is the aim of the present invention to provide a cuvette which can be produced in great numbers and with which the spectrometric equipment can be standardised regularly in order to compensate for gradual changes in the components. After exchange of a worn-out cuvette, the equipment must be readjusted followed by regular standardising of the equipment.

SUMMARY OF THE INVENTION

The invention relates to a cuvette for spectrometric analysis equipment, said cuvette having two opposing windows made of a material, which is transparent to the light of the waveband used for the analysis, said windows defining a limited light path of a light beam passing through a cavity inside the cuvette. According to the invention the cuvette is characterised in that the window surfaces forming the cuvette cavity are non parallel, thereby ensuring that the internal distances between opposed areas of the windows surfaces will vary across the transparent windows.

By these means it is ensured that the waves reflected internally in the cuvette cavity, will arrive in differing and substantially random phases, if they return to the transmitted main beam to be detected by the electronic detector means associated with the spectrometric equipment. In this way they will add to a sum of signals wherein tendencies to resonance are highly attenuated. Thereby the unwanted ripples in the spectrometric absorption diagram are avoided.

Preferably, one of the window surfaces—or at least one or more areas of the window surface—is arranged oblique, i.e. forming an angle slightly different from 0° with the other window surface. This is one way to ensure that the width of the cuvette cavity varies within a predetermined interval.

In a preferred embodiment according to the invention, the space between the two windows is wedge shaped. In the preferred embodiment according to the invention a wedge shaped spacer is arranged between and separating the two windows to define a slightly wedge shaped cuvette cavity. By these means, the unwanted ripples in the recorded spectra are almost avoided.

In an advantageous embodiment, at least one of the window surfaces is a slightly curved, e.g. a substantially spherical segment or almost spherical segment. The curved surface ensures that the width of the inner cavity varies with-in a predetermined interval.

Preferably, the material of the windows is diamond, Germanium, Zinc Selenium, Silicon or Gallium Arsenide. The windows may be coated by wear resistant coatings, such as hard carbon. The thickness of the spacer may vary from e.g. about 10 to 200 $\mu$m. Generally, the preferred thickness will depend on the properties of the medium or fluidum to be measured. In the case of raw milk or a dairy product, the preferred thickness of the spacer is about 20–50 $\mu$m.

According to the invention the thickness of the spacer may vary gradually "across" a diameter of the spacer—and along the periphery of the optical opening of the optical instrument. Preferably, the spacer is wedge shaped. The spacer may be made of several material, e.g. metal or plastic materials, depending on the conditions to which it will be subjected or exposed.

According to the invention a spacer may be produced in the following way: A sheet of metal film is submerged in an etching bath, such as ferric chloride, and the submergence depth is controlled and vaned by the time.

Preferably, the submergence depth is gradually increased until substantially the whole sheet is submerged and removed from the etching bath, or that substantially the whole sheet is submerged completely the submergence depth being gradually decreased until substantially the whole sheet is emerged and removed from the etching bath and that the submergence is time controlled. Preferably, the sheet of metal film has an original thickness of about 60 $\mu$m.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 8 shows a first and a second spectrum recorded with a cuvette filled with skim milk, and having an ordinary parallel spacer and an oblique spacer, respectively, between the windows.

FIG. 9 shows spectra recorded for three different cases.

DETAILED DESCRIPTION OF A PREFERRED EMBODIMENT

A cuvette according to the invention is designed for use in spectroscopic measuring apparatus, such as FTIR, and preferably MID IR. A preferred embodiment is specifically used to control dairy products. More specifically such apparatus is intended to continue being useful for a long lifetime albeit being exposed to high pressures and acid cleaning liquids used in dairy processes.

Figure 1:
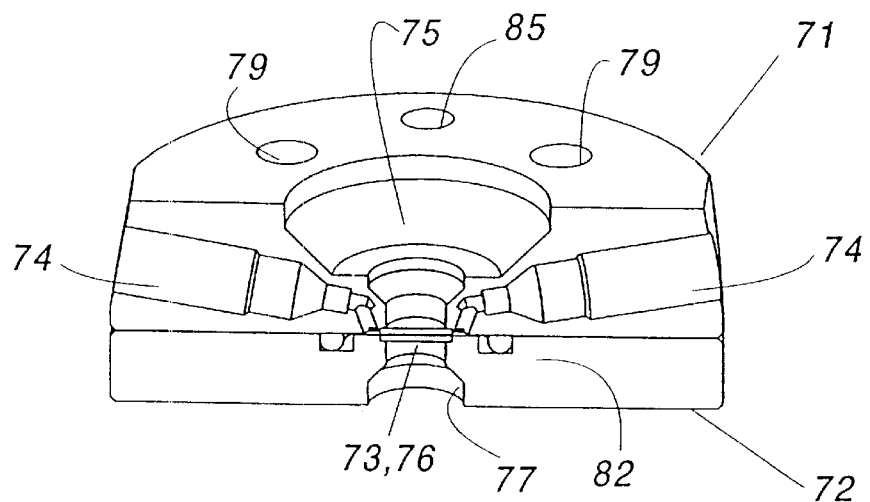
FIG. 1 shows a sectional view of a preferred embodiment of an IR cuvette according to the invention, seen from above, and in enlarged scale.
Figure 2:
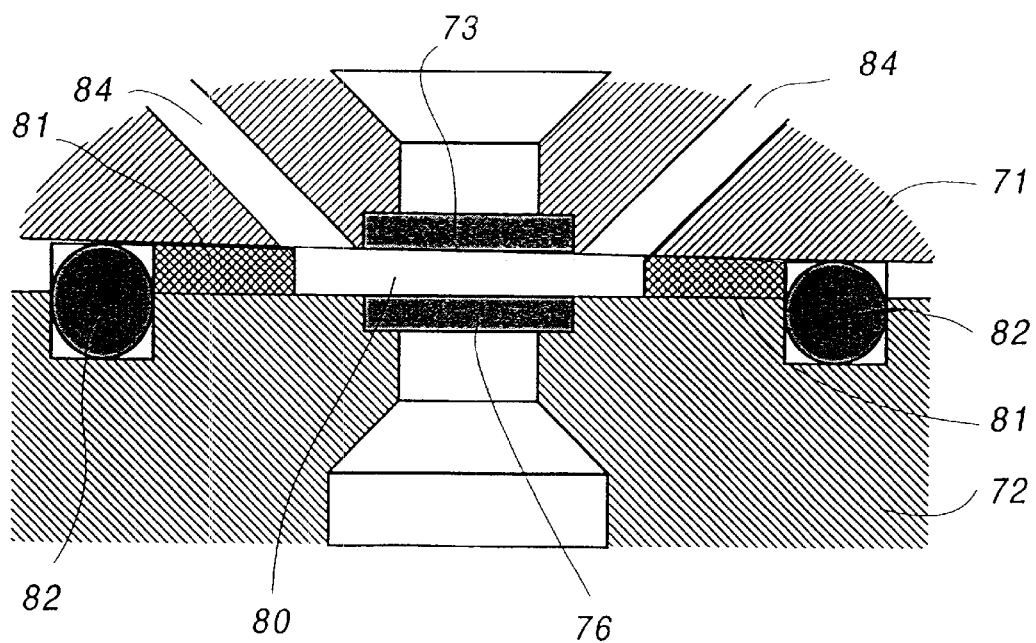
FIG. 2 shows an enlarged view of a centre portion of the cuvette in FIG. 1.

Such cuvettes may be made from steel provided with diamond windows. The price of diamonds has inspired the constructor to choose a structure having quite small diamond windows 73, 76, mounted between steel members 71, 72 and kept in a predetermined mutual distance by a thin spacer 81 (visible in the enlarged FIG. 2). FIG. 1 shows as an example a presently preferred embodiment of a cuvette. An IR light beam of the spectrometric equipment can pass through openings 75, 77 and diamond windows 73, 76 enclosing a small cavity 80 visible in FIG. 2. The cavity 80 is arranged to be filled with the fluid to be analysed through tiny tubes or channels 74, 84. Bore holes 79, 85 are arranged for the assemblage of the cuvette.

Preferably, the width of the fluid cavity and thereby the path length of the light beam within the cavity is about 20 to 50 μm. Diamond has a high refractive index compared to liquids such as water and milk. Therefore the two interfaces between windows and liquid are liable to cause multiple reflections whereby the cuvette cavity between the windows may become a sort of resonator, giving rise to a kind of ripple (many small peaks) in the recorded spectrum, e.g. as it appears from FIG. 8.

In order to avoid such multiple reflections it is suggested according to the invention that the window surfaces forming the cuvette cavity are non parallel, thereby ensuring that the internal distances between opposed areas of the window surfaces will vary across the transparent windows. In the preferred embodiment shown in FIG. 1 this is ensured by using a wedge shaped spacer 81 between the members 71, 72.

Figure 3:
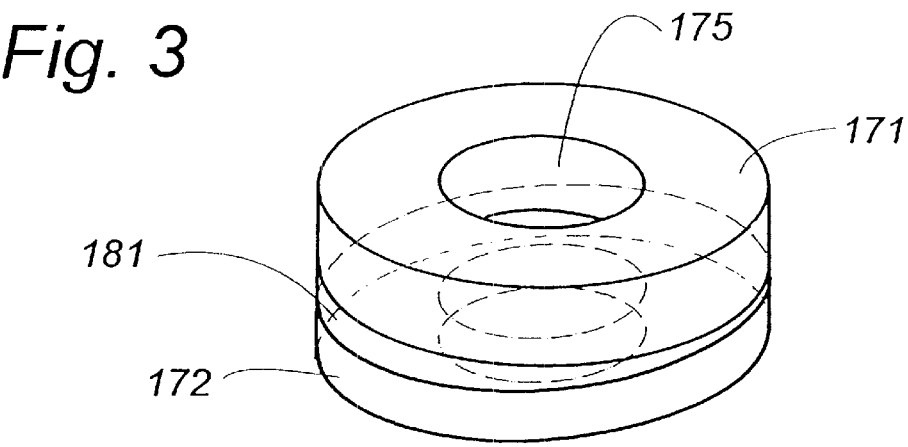
FIG. 3 shows a simplified view of an embodiment of an IR cuvette.
Figure 4:
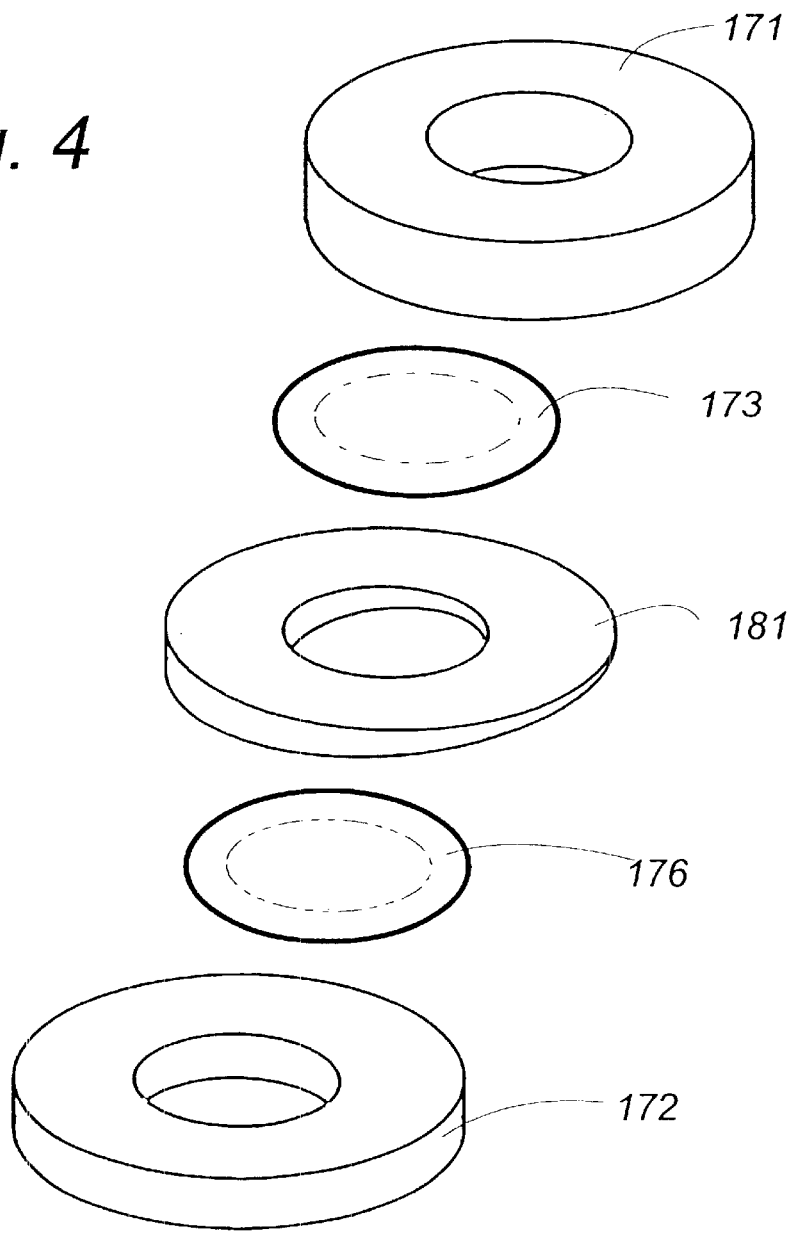
FIG. 4 shows an exploded view of the cuvette in FIG. 3 and a wedge shaped spacer.

FIG. 3 shows a simplified view of such a cuvette. For the sake of simplicity no fluid channels are shown in FIG. 3. FIG. 4 is an exploded view for clearly illustrating the structure. The thickness and wedge shape of the spacer 81 is strongly exaggerated for the sake of clarity. As it appears from FIGS. 3 and 4 the cuvette structure comprises top member 171 and bottom member 172. Between these members 171, 172 two diamond discs 173, 176 and a wedge shaped spacer 181 are inserted. The centre opening 180 in the spacer 181 provides the cavity to be filled with the fluid, e.g. milk. The outer peripheral rims of the discs 173, 176 abut the inner peripheral rims of the spacer 181 and the members 171, 172. In this way the dimensions of the cavity 80 are well defined and very stable.

For the purpose of illustrating the influence on a spectrum FIG. 8 shows a first spectrum 101 recorded for a skim milk filled cuvette having a ordinary plane parallel spacer between parallel windows substantially perpendicular to the optical axis of the optical spectrum recording system and a second spectrum 102 recorded for a skim milk filled cuvette having an oblique wedge shaped spacer between the windows still almost perpendicular to the optical axis of the optical spectrum recording system.

It appears clearly from this figure that a number of reflections occur when using the parallel windows. Such reflections are highly unwanted. They will deteriorate a standardisation of the apparatus, i.e. in the presence of such reflections, it will be impossible to standardise several apparatus in order to allow the use of the same standard calibration on all apparatus. Such standardisation is a great advantage when the apparatus are produced and distributed in great numbers to many world-wide spread laboratories.

The effect of using an oblique or wedge shaped spacer may be explained as follows: With parallel windows the result (at some wavelengths) of the light beams reflected within and passing through the cavity defined by the centre area of the spacer may be a constructive interference, providing large ripples in the spectrum. Using oblique windows, the length of the light path will vary from top to bottom of the spacer. Thereby the result will be a sum of many differing (almost random) wave patterns providing hardly any or at least much smaller ripples.

In a second embodiment the cuvette windows are made from Germanium coated with hard carbon. FIG. 9 illustrates the influence of using a wedge shaped spacer between coated Germanium windows. The cuvette was filled with air. The heavily varying curve track 201 shows a spectrometric recording using an ordinary parallel spacer. The less varying curve track 202 shows a spectrometric recording using a first wedge shaped spacer providing a 16% variation in light path from top to bottom of the optical window. The almost non-varying curve track 203 shows a spectrometric recording using a second wedge shaped spacer, providing a 27% variation in light path from top to bottom of the optical window.

It is believed that even small imperfections, such as non parallel surfaces, or non plane surfaces will contribute to attenuate the ripples. However to obtain a reasonable flat curve as 203 in FIG. 9 it is recommended that the light path vanes a great deal e.g. about 20–30%.

Figure 7A:
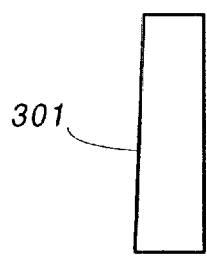
FIGS. 7A, 7B, 7C, 7D, 7E and 7F show transverse sections through different cavities according to the invention.
Figure 7B:
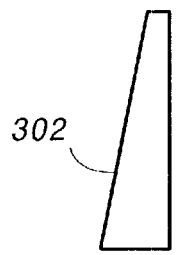
Figure 7C:
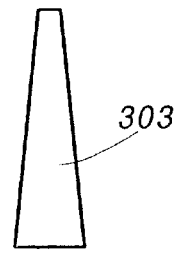

FIGS. 7A–7F illustrate the principles of the invention by diagrams showing highly exaggerated sections or contours of various embodiments of cuvette cavities. In the preferred embodiment the cuvette cavity is slightly wedge shaped. One (301) of the window surfaces defining the cavity is oblique. The other is substantially upright (FIG. 7A). For the sake of clarity FIG. 7B indicates the wedge form highly exaggerated by showing a window surface 302 being clearly oblique. FIG. 7C indicates that both window surfaces of a cavity 303 may be oblique.

Figure 7D:
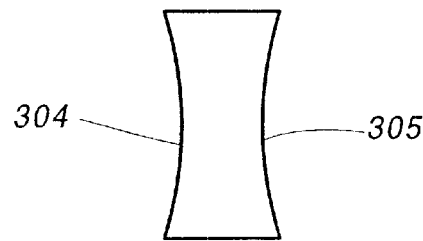
Figure 7E:
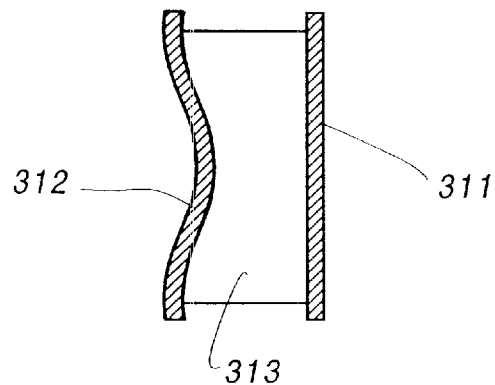

However, the essential feature is that the light paths within the cuvette must be of various lengths. This can be accomplished in many ways. One or both of the window surfaces 304, 305 in the cavity may be curved, e.g. a convex curvature (FIG. 7D). They may be any kind of curved section, such as a spherical segment, a parabolic segment, hyperbolic segments or surfaces composed thereof. A presently contemplated cavity 313 is defined by a plane window 311 and a curved window 312. The curved window surface almost resembles a spherical segment surrounded by an annular spherical element of opposite curvature; (i.e. a radial section through the curved surface is almost sinusoidal as shown in FIG. 7E). This provide the curved window 312 with a substantially plane annular periphery able to be mounted in the cuvette in the same way as an ordinary plane window.

Figure 7F:
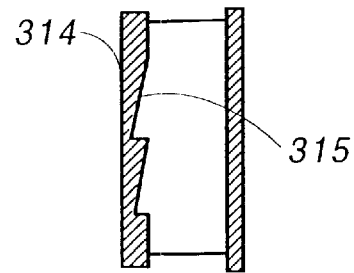

In a further contemplated embodiment (with or without a spacer) at least one area of a surface of a window 314 has been processed, e.g. by grinding, thereby providing a number of slightly oblique areas 315 in the window surface, e.g. as shown in FIG. 7F.

Figure 5:
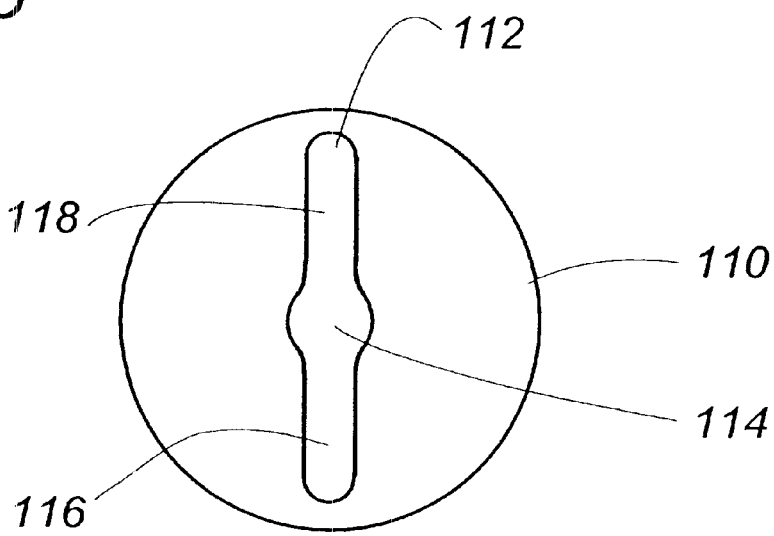
FIG. 5 shows as an example a first preferred embodiment of a spacer.
Figure 6:
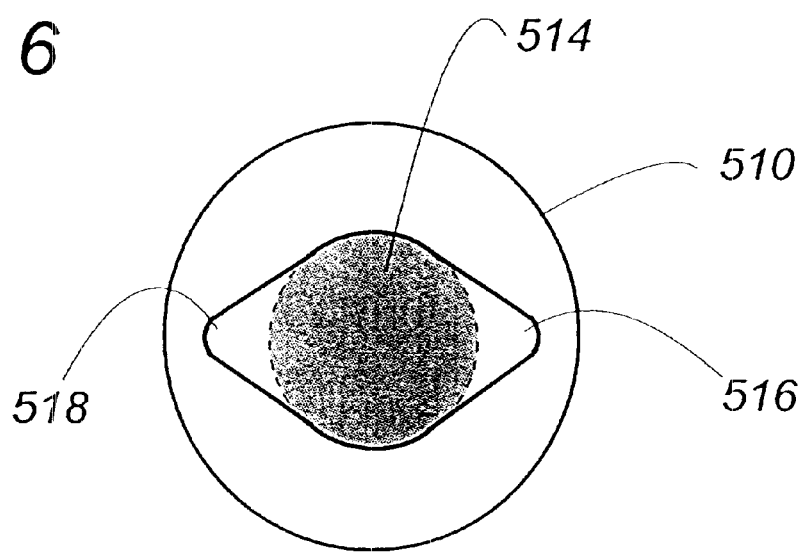
FIG. 6 shows as an example a second preferred embodiment of a spacer.

The most simple way to obtain a cuvette cavity providing light paths of various lengths seems to be by use of a wedge shaped spacer between the windows. Presently preferred embodiments of a wedge shaped spacer according to the invention are shown in FIGS. 5 and 6. Each of the spacers is designed for use in a specific flow cuvette.

In FIG. 5 the spacer 110 is shown as a circular disc. It is provided with a longitudinal sloth 112 comprising a circular portion 114 defining the cavity of the cuvette, i.e. the zone within the cuvette, which is filled with the liquid sample to be measured. The two adjacent portions 116 and 118 of the sloth 112 provide for the inlet and outlet of liquid to and from the cavity 114. In a first embodiment such a spacer may have a diameter of 5.2 mm, the diameter of the inner cavity can be 2.2 mm and the thickness may vary from 30 $\mu$m to 45 $\mu$m. In a second embodiment of similar structure the outer diameter may be 19.5 mm, the diameter of the inner cavity can be 5.0 mm and the thickness may vary from 22 $\mu$m to 54 $\mu$m.

In a further embodiment shown in FIG. 6, the spacer 510 has an almost circular portion 514 on a substantially rhombic opening. The two corners 516 and 518 of the rhombus form the inlet and outlet for fluid. The diameter of spacer may be 21 mm. The diameter of the circular portion of the opening is 10 mm. The disc is preferably wedge shaped, the thickness varying from about 28 $\mu$m to 48 $\mu$m at the outer periphery of the disc. Accordingly, the variation across the cavity will be about 10 $\mu$m.

In the preferred embodiment, the spacer is intended for the MID-IR-range. The light path through the cuvette may be from 10 to 100, even 200 $\mu$m. In the preferred embodiment it is from 25 to 50 $\mu$m, e.g. having an average of about 38 $\mu$m.

Accordingly the spacer is very thin, about said 38 $\mu$m thick. According to the invention the spacer is wedge shaped, e.g. it may be 22 $\mu$m in the upper end and 54 $\mu$m in the lower end of the periphery of the disc. (difference: 32 $\mu$m) When looking strictly at the optical light path through the cuvette—the light path varies from about 34 to 42 $\mu$m across the 5 mm cavity. (i.e. a variation of 8 $\mu$m/38 $\mu$m or +/−4 $\mu$m on 38 $\mu$m which is about +/−10% or close to 20%)

A spacer according to the invention may be produced from several materials such as metals or plastic materials depending on the conditions the cuvette is exposed to. However the presently preferred material is a 60 $\mu$m metal film, preferably a film having a photographic coating. As it is well-known from the production of printed circuits such coating can be used for controlled etching in an etching bath, comprising e.g. Ferric chloride.

According to the invention the metal film is exposed to a gradually varying and controlled etching providing a slightly wedge shaped metal sheet. According to a first preferred method the metal film is submerged in an etching bath. Preferably the metal film is submerged gradually and slowly as time passes by,—and then retracted completely from the etching bath or visa versa. Furthermore the film might be both submerged and retracted gradually. In either way a wedge shaped film is the result. The temperature of the bath can be 48° C., and the submergence rate can be 1 mm per minute. Preferably the film is submerged or partly submerged for about 20 minutes in the etching bath. Preferably the etching fluid is stirred thoroughly. According to a second embodiment the coated metal film is exposed to a series of jets of etching liquid, whereby a covering sheet, or screen may be gradually moved to vary the area hit by the etching liquid.

Afterwards the final thickness profile of the sheet is measured. The useful areas are located and a template of the desired form is transferred to the photographic coating. The desired form of the spacer is cut out of the wedge shaped foil e.g. either by a further etching now controlled by the remaining portion of the photographic coating or by punching or stamping.

Alternatively, either the metal film sheet or the cut-out spacer may be subjected to a controlled grinding process e.g. by a diamond paste in order to achieve the desired wedge form. In a further alternative embodiment one or both of the windows are subjected to a controlled grinding process in order to achieve a desired wedge form, which in turn will ensure a wedge shaped cavity. In a further alternative embodiment an oblique mounting of one or both of the windows in the cuvette steel members may be arranged in order to ensure a wedge shaped cavity.

The diamond windows may be made from natural or artificial/industrial diamonds, such as CVD-diamonds. In a further embodiment, the windows are made from Germanium provided with a hard carbon coating applied by chemical vapour deposition. Other window materials could be Silicon or Gallium Arsenide.

The invention is described in the above in way of non-limiting examples. It is understood that one skilled in the art can accomplish variants without departing from the spirit and scope of the invention as defined in the claims. In particular he may roll or press the plastic film or metal foil into the wedge form.

What is claimed is:

1. A cuvette for a spectrometric analysis equipment, said cuvette having two opposing windows made of a material, which is transparent to the light of the waveband used for the analysis, said windows defining a limited light path of a light beam passing through a cavity inside the cuvette, where a wedge-shaped spacer is inserted between and separating the two windows, the spacer surrounding the cuvette cavity, and defining the cavity between the two windows, wherein the length of the light path within the cavity is between 10 $\mu$m and 200 $\mu$m.

2. The cuvette according to claim 1, wherein the cuvette is for analysis of fluid samples.

3. The cuvette according to claim 1, wherein the refractive index of the windows differs considerably from the refractive index of the fluid sample.

4. The cuvette according to claim 1, wherein the material of the windows is Diamond, Germanium, Zinc Selenium, Silicon or Gallium Arsenide.

5. The cuvette according to claim 1, wherein the object to be measured is raw milk or a dairy product.

6. The cuvette according to claim 1, wherein the cuvette is intended for MID-IR waveband, wherein the path length between the two windows varies about 20%–30% across the optical window.

7. The cuvette according to claim 1, wherein the cuvette is intended for MID-IR waveband, wherein the path length between the two windows varies from about 10–200 μm across the optical window.

8. The cuvette according to claim 1, wherein the cuvette is intended for MID-IR waveband, wherein the path length between the two windows varies from about 22 μm to about 54 μm across the optical window.

9. A spacer for the cuvette according to claim 1, wherein the thickness of the spacer is from about 10 to 200 μm, varying gradually across a diameter of the spacer and/or along the periphery of the optical opening of the optical instrument.

* * * * *